United States Patent
Paladini et al.

(10) Patent No.: US 9,370,332 B2
(45) Date of Patent: Jun. 21, 2016

(54) ROBOTIC NAVIGATED NUCLEAR PROBE IMAGING

(75) Inventors: Gianluca Paladini, Skillman, NJ (US); Ali Kamen, Skillman, NJ (US); Oliver Kutter, Hartheim (DE)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 100 days.

(21) Appl. No.: 13/881,209

(22) PCT Filed: Nov. 10, 2011

(86) PCT No.: PCT/US2011/060091
§ 371 (c)(1),
(2), (4) Date: Jun. 11, 2013

(87) PCT Pub. No.: WO2012/064917
PCT Pub. Date: May 18, 2012

(65) Prior Publication Data
US 2013/0261446 A1    Oct. 3, 2013

Related U.S. Application Data (60) Provisional application No. 61/411,951, filed on Nov. 10, 2010.

(51) Int. Cl.
*A61B 6/00* (2006.01)
*A61B 5/00* (2006.01)
*A61B 6/03* (2006.01)

(52) U.S. Cl.
CPC ............. *A61B 6/4458* (2013.01); *A61B 5/0064* (2013.01); *A61B 6/037* (2013.01); *A61B 6/4258* (2013.01); *A61B 6/4417* (2013.01); *A61B 6/4464* (2013.01); *A61B 6/466* (2013.01); *A61B 6/481* (2013.01); *A61B 6/5223* (2013.01); *A61B 6/5229* (2013.01); *A61B 6/4057* (2013.01); *A61B 6/5247* (2013.01)

(58) Field of Classification Search
None
See application file for complete search history.

(56) References Cited

U.S. PATENT DOCUMENTS 4,632,123 A * 12/1986 Govaert et al. ................. 600/436
5,452,721 A *  9/1995 Hacker ........................ 600/436

(Continued)

FOREIGN PATENT DOCUMENTS

EP        1700568 A2      9/2006
WO   WO 2007131561 A2   11/2007

OTHER PUBLICATIONS

Vermeeren et al., "Intraoperative Radioguidance With a Portable Gamma Camera: a novel technique for laparoscopic sentinel node localisation in urological malignancies." Eur. J. Med. Mol. Imaging (2009), vol. 36, pp. 1029-1036.*

*Primary Examiner* — James Kish (57) ABSTRACT

Robotic navigation is provided for nuclear probe imaging. Using a three-dimensional scanner (19), the surface of a patient is determined (42). A calibrated robotic system positions (48) a nuclear probe about the patient based on the surface. The positioning (48) may be without contacting the patient and the surface may be used in reconstruction to account for spacing of the probe from the patient. By using the robotic system for positioning (48), the speed, resolution and/or quality of the reconstructed image may be predetermined, user settable, and/or improved compared to manual scanning. The reconstruction (52) may be more computationally efficient by providing for regular spacing of radiation detection locations within the volume.

21 Claims, 3 Drawing Sheets

(56) References Cited

U.S. PATENT DOCUMENTS

| | | | |
|---|---|---|---|
| 7,750,311 B2* | 7/2010 | Daghighian | 250/398 |
| 7,826,889 B2* | 11/2010 | David et al. | 600/436 |
| 8,050,743 B2* | 11/2011 | Daghighian | 600/431 |
| 8,183,532 B2* | 5/2012 | Goedicke et al. | 250/363.04 |
| 8,200,508 B2* | 6/2012 | Fujita et al. | 705/3 |
| 8,338,788 B2* | 12/2012 | Zilberstein et al. | 250/363.04 |
| 8,489,176 B1* | 7/2013 | Ben-David et al. | 600/436 |
| 8,565,860 B2* | 10/2013 | Kimchy et al. | 600/436 |
| 8,748,827 B2* | 6/2014 | Zilberstein et al. | 250/363.04 |
| 2001/0056234 A1* | 12/2001 | Weinberg | 600/436 |
| 2004/0054248 A1* | 3/2004 | Kimchy et al. | 600/3 |
| 2005/0055174 A1* | 3/2005 | David et al. | 702/152 |
| 2006/0261277 A1* | 11/2006 | D'Ambrosio et al. | 250/363.05 |
| 2008/0230704 A1* | 9/2008 | Daghighian | 250/363.03 |
| 2008/0277591 A1* | 11/2008 | Shahar et al. | 250/394 |
| 2009/0152471 A1* | 6/2009 | Rousso et al. | 250/363.04 |
| 2010/0046817 A1* | 2/2010 | Goedicke et al. | 382/131 |
| 2010/0061509 A1* | 3/2010 | D'Ambrosio et al. | 378/62 |
| 2010/0219346 A1* | 9/2010 | Daghighian | 250/363.03 |
| 2011/0026685 A1* | 2/2011 | Zilberstein et al. | 378/197 |
| 2011/0286576 A1* | 11/2011 | Cui et al. | 378/62 |

* cited by examiner

ROBOTIC NAVIGATED NUCLEAR PROBE IMAGING

RELATED APPLICATIONS

The present patent document claims the benefit of the filing date under 35 U.S.C. §119(e) of Provisional U.S. Patent Application Ser. No. 61/411,951, filed Nov. 10, 2010, which is hereby incorporated by reference.

BACKGROUND

The present embodiments relate to medical imaging. In particular, imaging with a nuclear probe is provided.

Diagnostic medical modalities, such as computed tomography (CT), magnetic resonance (MR), and ultrasound acquire detailed images. The images depict anatomical structures, such as location of internal organs and tumors. Other modalities, such as positron emission tomography (PET) and single positron emission computed tomography (SPECT), may visualize functional changes or information. PET and SPECT may show areas of cancerous growth or other operation of anatomy, but with less or no details about the surrounding anatomy.

These imaging modalities may not be usable during a surgical procedure. For 3D tomography scanning procedures, a patient lies on a motorized bed which moves inside a doughnut-shaped image acquisition device. The device limits surgical access. Scanning with such large complex systems may be expensive.

In nuclear medicine, hand-held nuclear activity devices, such as a gamma probe or a beta probe, are capable of detecting the uptake of injected tumor-seeking radiopharmaceuticals. Gamma probes, for example, are used in parathyroid and sentinel lymph node surgery, where the gamma probes provide an audible signal to locate regions where injected radionuclides are present. The locations detected with a gamma probe may be visualized rather than just relying on an audible signal. A tracking system measures the position of the gamma probe while acquiring data to compute the images. The user manually positions the gamma probe against the patient's skin for detection. Such images may then be fused with image data coming from other detectors. For example, images produced with an optically-tracked gamma probe are fused together with images from a video camera calibrated into the same coordinate space. The resulting fused image shows the location of sentinel lymph nodes overlaid onto the patient's skin, providing guidance to surgeons. However, optical tracking of the hand-held probe requires calibration based on marker positions and suffers from limited accuracy. Reconstruction from the acquire projection data is complicated by the manual positioning of the gamma probe. The reconstructed image may have inadequate quality, requiring the process to be performed again. Since radionuclides are involved, repetition may be undesired.

BRIEF SUMMARY

By way of introduction, the preferred embodiments described below include methods, systems, instructions, and computer readable media for robotic navigation in nuclear probe imaging. Using a three-dimensional scanner, the surface of a patient is determined. A calibrated robotic system positions a nuclear probe about the patient based on the surface. The positioning may be without contacting the patient, and the surface may be used in reconstruction to account for spacing of the probe from the patient. By using the robotic system for positioning, the speed, resolution and/or quality of the reconstructed image may be predetermined, user settable, and/or improved compared to manual scanning. The reconstruction may be more computationally efficient by providing for regular spacing of radiation detection locations within the volume.

In a first aspect, a system is provided for robotic navigation in nuclear probe imaging. A robotic assembly connects with a nuclear detector for detecting radiation. The robotic assembly is operable to move the nuclear detector relative to a patient. A three-dimensional scanner is positioned to view the patient. A processor is configured to control movement of the robotic assembly to scan the patient with the nuclear detector in a pattern. The movement is a function of the view of the patient by the three-dimensional scanner.

In a second aspect, a method is provided for robotic navigation in nuclear probe imaging. A three-dimensional surface of a patient is identified. A detector is moved to regularly spaced locations about the patient based on the three-dimensional surface. The moving avoids contact with the patient by the detector. Radiation is detected with the detector at the regularly spaced locations. The detector is aligned such that the radiation being detected is from within the patient. A volume is reconstructed from the radiation. The volume represents the patient. An image of the reconstructed volume is displayed.

In a third aspect, a non-transitory computer readable storage medium has stored therein data representing instructions executable by a programmed processor for robotic navigation in nuclear probe imaging. The storage medium includes instructions for receiving a user indication of resolution selection, robotically positioning a nuclear probe as a function of the resolution selection, receiving radiation projection information from the nuclear probe for different positions from the positioning, and reconstructing an image from the radiation projection information.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Cancerous lesions that are visible based on uptake of radiotracer agents may be identified. By providing detection of uptake during a surgical procedure, the surgeon may be assisted in resecting lesions. For example, positive lymph nodes are resected from a patient's breast using, in part, detection of the radiotracer agents. A robotic system positioning a probe acquires data in real-time with the surgical operation. The robotic system is less spatially limiting than a PET/SPECT scanner, allowing use during surgery. Accurate sentinel lymph node (SLN) mapping, localization, and characterization may be important in staging the cancer and individualizing cancer treatment for maximum benefit.

The robotic system automatically performs the scanning procedure for reconstruction. For example, a robot positions a detector to collect spatial samples from the region of interest on the patient. Automatic navigation of a collimated nuclear probe may assist with mapping, localization and characterization. Automatic scanning of the patient anatomy may enhance reconstruction quality due to better (denser) and more regularly or evenly spaced sampling. The robotic scanning may provide for quicker sampling.

The automated scanning using the robot may be further assisted by a three-dimensional scanner. For example, a time-of-flight camera models the patient's skin surface. The position of the probe is guided about the surface, such as being positioned at a particular distance from the patient in each location in a regular sampling grid. The surface may be used to limit reconstruction, allowing for more efficient tomographic reconstruction.

Figure 1:
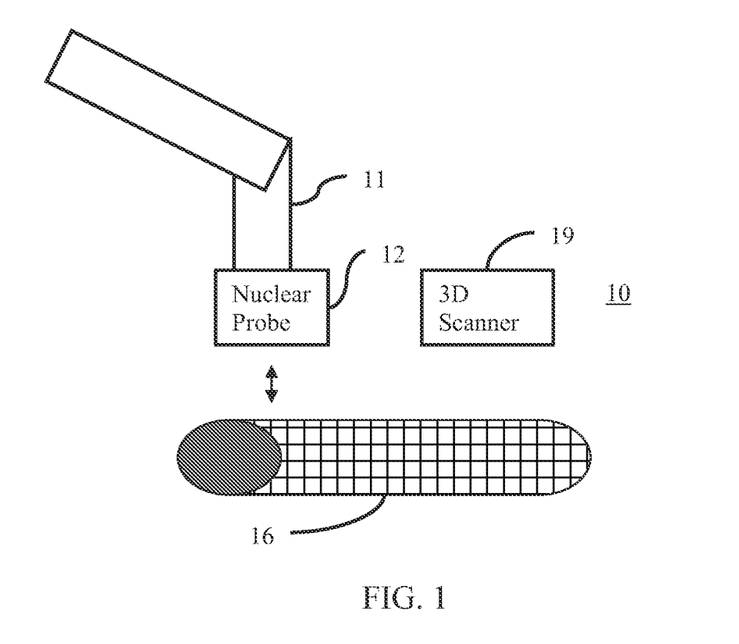
FIG. 1 is an illustration of one embodiment of an arrangement for robotic navigation in nuclear probe imaging.
Figure 2:
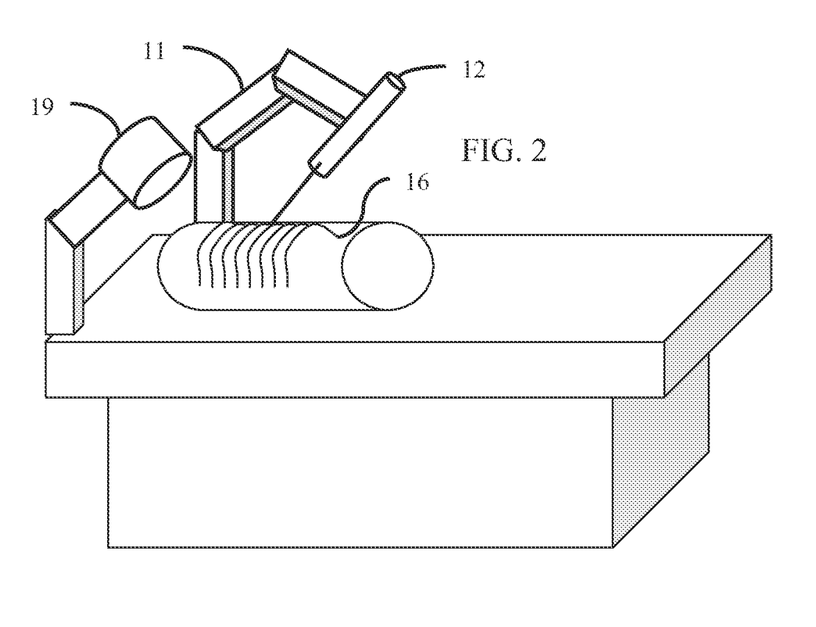
FIG. 2 is an illustration of another embodiment of an arrangement for robotic navigation in nuclear probe imaging.
Figure 3:
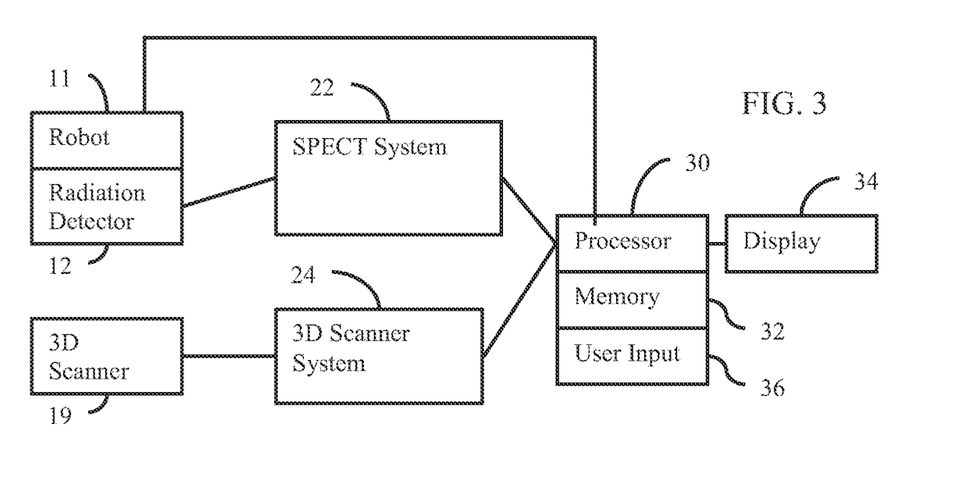
FIG. 3 is a block diagram of a system for robotic navigation in nuclear probe imaging, according to one embodiment.

FIGS. 1-3 show different embodiments of a system for robotic navigation in nuclear probe imaging. FIGS. 1 and 2 show the arrangement of the robotic assembly 11, nuclear probe 12, and 3D scanner 19 with different scan patterns 16 on a patient. FIG. 3 shows a system with the robotic assembly 11, nuclear probe 12, and 3D scanner 19 connected to processing components for control, user interaction, and/or display.

The system of FIG. 3 includes the robotic assembly 11, nuclear probe 12, a single photon emission computed tomography (SPECT) system 22 with a detector 26, a three-dimensional scanner 19, a three-dimensional scanner system 24, a processor 30, a memory 32, a user input 36, and a display 34. Additional, different, or fewer components may be provided. For example, a network or network connection is provided, such as for networking with a medical imaging network or data archival system. As another example, a preoperative imaging system, such as a computed tomography or magnetic resonance imaging system, is provided. In another example, the processor 30 is part of or also performs the functions of the SPECT system 22 and/or three-dimensional scanner system 24. In yet another example, the detector 26 is in the housing of the nuclear probe 12.

The memory 32, user input 36, processor 30, and display 34 are part of a medical imaging system, such as the three-dimensional scanning system 24, SPECT system 22, x-ray, computed tomography, magnetic resonance, positron emission, or other system. Alternatively, the memory 32, user input 36, processor 30, and display 34 are part of an archival and/or image processing system, such as associated with a medical records database workstation or server. In other embodiments, the memory 32, user input 36, processor 30, and display 34 are a personal computer, such as desktop or laptop, a workstation, a server, a network, or combinations thereof.

The nuclear probe 12 is a nuclear detector for detecting radiation. The nuclear probe 12 is a gamma, beta, or other probe for detecting radiation. For example, the nuclear probe 12 includes a Geiger-Muller tube or scintillation counter for detecting radiation following interstitial injection of a radionuclide. The nuclear probe 12 has a single detector and generally pencil shape. Alternatively, an array of detectors may be provided, and/or other shapes may be used.

As shown in FIG. 3, the nuclear probe 12 electrically connects with the SPECT system 22. For connection with the SPECT system 22, a single coaxial or other cable is provided. As shown in FIGS. 1 and 2, the nuclear probe 12 physically connects with the robotic assembly 11. The robotic assembly 11 holds, carries, releasably attaches to, fixedly includes, is formed on, around or against, or otherwise connects with the nuclear probe 12.

The nuclear probe 12 is configured to detect radiation along a line. Radiation signals (e.g., gamma rays or light caused by gamma rays) are converted to electrical energy. The detector detects radiation from the beam region. Radionuclides emit gamma radiation or emitted positrons cause release of gamma radiation.

The probe 12 is directional. The sensitive region for detecting radiation is in a beam or cone along a line extending from the nuclear probe 12. The beam is converging, collimated, and/or diverging. Any radiation emitted within the sensitive region is detected. For example, radiation emitted from within a cone shaped region extending from the nuclear probe 12 is detected. The nuclear probe 12 does not resolve the depth or distance from the radiation source and the probe 12. The nuclear probe 12 may not indicate the lateral position within the beam of the source of radiation. Accordingly, the detected radiation is a projection of radiation sources within the beam at a given detection time. Readings are taken for each position of the probe 12 as the probe 12 is moved, providing a projection type sampling of the radiation over a three-dimensional volume.

The projections along lines originating at different locations and/or at different angles within the volume are detected. Where an array of detectors is used, depth information may be received. Where the single element is tilted at different angles and the probe 12 is moved, the radiation distribution in three-dimensions may be measured.

In alternative embodiments, an ultrasound transducer is used instead of the nuclear probe. Acoustic energy is used to detect lesions or other potentially cancerous regions of the patient. In another alternative embodiment, skin cancer detection or screening is provided using non-invasive optical or thermal imaging. The images of skin are acquired with a camera or other device replacing the nuclear probe 12. The images are registered or aligned with images from the three-dimensional scanner 19. The surface of the patient is acquired in multiple acquisitions over time and, the three-dimensional texture is mapped to visualize the skin surface.

The SPECT system 22 includes a computer (e.g., the processor 30) for reconstructing the radiation detected at the probe 12. The SPECT system 22 is a standalone device, such as a full SPECT system, a workstation, or a computer. Alternatively, one or more processors of the three-dimensional scanner system 24 perform the reconstruction without other devices. The SPECT system 22 may be implemented in the processor 30 without a separate device. In other embodiments, a positron emission tomography (PET) system is used instead of the SPECT system 22.

The robotic assembly 11 connects with and moves the nuclear probe 12. The robotic assembly 11 includes one or more robot arms and joints. One of the robot arms connects with the nuclear probe 12, either directly or indirectly (e.g., through a joint, extension, or other devices connected with the arm). The robotic assembly 11 includes a base configured to be stationary during movement of the robot arm and relative to the three-dimensional scanner 39 and/or patient. The base may be a plate or other structure fixed to the floor, wall, ceiling, or patient table. FIG. 1 shows the robotic assembly 11 with a ceiling mount. FIG. 2 shows the robotic assembly 11 with a floor or patient table mount. Alternatively, the base is moveable, such as being on a track.

An active robotic assembly 11 is used, such as including sensors, motors, and controllers for positioning the probe 12. The robotic assembly 11 positions the nuclear probe 12 at different positions relative to the patient. For radiation detection, the positions may be spaced slightly away from the patient. FIG. 1 shows a double arrow representing the probe 12 being positioned out of contact with the patient, such as at one or more centimeters (e.g., 5-20 centimeters). Other distances may be used, such as greater distances to avoid interference with ongoing surgery. The relative position of the probe 12 may be indicated by the robotic sensors instead of or in addition to data from the three-dimensional scanner 19.

In one example embodiment, the probe 12 is mounted onto an articulated robot arm rather than being used free-hand. The probe's motion trajectory may be planned and known upfront, rather than being computed from freehand motion subject to inaccuracies. Fully-automated scanning and/or treatment may be provided. For example, the robot arm moves the nuclear probe 12 by hovering over the patient in a pre-defined pattern, without needing to touch the patient's skin. The probe 12 is moved over a motion path that can be used to produce a 2D and/or 3D SPECT reconstruction. The automated movement may provide a fixed or regular pattern of detection, allowing for computationally more efficient reconstruction as compared to free-hand movement. Greater accuracy and/or quality of image data may result. A 2D or 3D map of locations of higher radionuclide uptake ("hotspots") are detected and visualized. An optional registration step with pre-acquired 3D PET/SPECT may further enhance the reconstruction results, providing anatomy information associated with the detected radiation.

In an alternative embodiment, the robotic assembly 11 is or includes a raster scanner arrangement. A pan and a tilt stage form the raster scanner arrangement. The nuclear probe 12 is mounted within or on the pan. The mount is moveable, allowing the nuclear probe 12 to be laterally positioned along one or two-dimensions within the pan. The tilt stage connects with the pan or connects to the nuclear probe 12. The tilt stage changes the angle of the pan and/or nuclear probe 12 relative to the patient. By translation within the pan and/or tilting, radiation may be detected along different lines through a volume of the patient. The raster scanner is positioned manually or automatically (e.g., using a track and/or arm and joint arrangement) above, beside, against, or adjacent to the patient for detecting radiation.

The three-dimensional scanner 19 is a time-of-flight camera. For example, a modulated optical signal is transmitted by a transmitter to illuminate the patient. The reflected light is detected by a semiconductor sensor, which is able to determine the time-of-flight for each pixel. Complete three-dimensional information (e.g., lateral as well as depth) is captured in parallel. In alternative embodiments, other structured or modulated light systems are used to acquire three-dimensional information representing the surface of the patient. In other embodiments, stereo view, triangulated laser dot or pattern, stereoscopic depth or other optical technique and system for detecting a three-dimensional surface is used. Non-optical techniques, such as ultrasound, may be used.

The three-dimensional scanner 19 is positioned to view the patient. The scanner 19 may be positioned to view the nuclear probe 12, at least when the probe 12 is positioned about the patient to detect radiation. Alternatively, the scanner 19 is positioned to view the patient with as little interference from the robotic assembly 11 and the nuclear probe 12 as possible, such as being above the patient and on an opposite side of the patient than the robotic assembly 11.

The three-dimensional scanner 19 scans the patient, such as scanning the patient's skin. Any part of the patient within the field of view of the three-dimensional scanner is scanned. The field of view may be adjusted, such as by changing optics and/or by repositioning the scanner 19 (e.g., robotic positioning of the scanner 19).

The three-dimensional scanner system 24 is a processor, circuit, application specific integrated circuit or other device for determining three-dimensional coordinate points from the data (e.g., image or images) acquired from the scanner 19. The three-dimensional scanner system 24 determines the x, y, and z (Cartesian coordinates) or range, angle 1, and angle 2 (polar coordinates) of different locations on the patient. A surface results from or is fit to the three-dimensional scanning. Alternatively, the coordinates for the points are determined as the surface without separately defining a full surface.

The surface representing the patient is acquired automatically or without user indication of specific points on the patient. This may avoid contact with exposed tissue or tissue to be operated on, reducing risk to the patient. Obtaining the surface with the three-dimensional scanner 19 may provide for faster surface identification compared with systems using manual point indication on the patient (i.e., non-3D scanning). Alternatively, the user may indicate particular points on the patient, such as placing markings or an object against, on, or in the patient.

The user input 36 is a button, a keyboard, a rocker, a joy stick, a trackball, a voice recognition circuit, a mouse, a touch pad, a touch screen, sliders, switches, combinations thereof, or any other input device for sending commands. For example, the user input 36 is a mouse or trackball with associated buttons for indicating a region of interest on an image. A pointer is positioned to indicate diagonally opposite corners for a quadrangular region of interest, points on a border for any shaped region, or tracing of the entire border. Button activation is used to indicate selection of particular points at the pointer location. A region of interest may be extrapolated or interpolated from the user selected points. Edge detection based on the user indicated points may be used to complete the region designation.

The region is designated on an image from any source. The image may be a rendering of the three-dimensional surface from the scanner system 24, allowing the user to indicate the region of interest on the patient from the three-dimensional surface. The user input 36 and processor 30 receive the user input information.

The processor 30 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for calibrating, controlling the robotic assembly 11, controlling the detection of radiation, controlling the detection of the surface, reconstruction, and/or image generation. The processor 30 is a single device or multiple devices operating in serial, parallel, or separately. The processor 30 may be a main processor of a computer, such as a laptop or desktop computer, or may be a processor for handling some tasks in a larger system, such as in an imaging system (e.g., SPECT system 22 or scanner system 24). Based on hardware, software, or combinations thereof, the processor 30 is configured to implement instructions or perform acts.

In one embodiment, the processor 30 is configured to calibrate the robotic assembly 11 with the three-dimensional scanner 19. The calibration occurs first, such as just before surgery. The calibration may be performed before a patient is brought into the room, but may be performed with a patient on the table. The calibration occurs once or more, such as calibrating once a week, once a month, once a day, or only once. Calibration may be performed as needed, when triggered or performed periodically.

The calibration aligns the coordinate system of the robotic assembly 11 and corresponding nuclear probe 12 with the coordinate system of the three-dimensional scanner 19. The calibration determines a transformation that maps the three-dimensional scanner coordinate system to that of the robotic assembly 11 and nuclear probe 12 or vise versa. By positioning the nuclear probe 12 to specific locations viewable by the scanner 19, the transformation may be determined. For example, three or more locations on a patient table are used. In another example, a device, such as a cube, is positioned on the patient table. The robotic assembly 11 positions the probe 12 against or relative to the device at various locations. The scanner 19 scans the probe 12 and the device. The processor 30 determines the transformation from the image of the scanner 19 and the position information from the robotic assembly 11. The calibration procedure may be implemented by having the robot end-effector without the probe 12 touching known points in space where the points are also identified from the three-dimensional scanner measurements.

The processor 30 is configured to control movement of the robotic assembly 11 to scan the patient with the nuclear probe 12. The processor 30 instructs the robotic assembly 11 to position the nuclear probe 12 at different positions. The processor 30 feeds coordinates and/or directions and amounts of movement to the robotic assembly 11. Alternatively, the processor 30 sends commands to specific motors, joints, encoders, sensors or other components of the robotic assembly 11 to control the specific components. The robotic assembly 11 operates based on the instructions to move the nuclear probe 12 to specific locations.

The processor 30 controls each movement individually. Alternatively, the processor 30 sends a sequence of movements or a reference to a specific sequence of movements. The robotic assembly 11 moves, based on control from the processor 30, the nuclear probe 12 to different locations for obtaining radiation readings along different lines or beams through the patient.

Based on the control, the robotic assembly 11 moves the nuclear probe 12 in a pattern. The pattern is defined by locations and angles from which the nuclear probe 12 detects radiation. For each location in three-dimensional space, the nuclear probe 12 is oriented at a particular direction towards the patient. A projection reading along the corresponding line is performed. At the same location, another reading may be performed with the nuclear probe 12 at a different angle, reading along a different line. This change in angle or a change in three-dimensional coordinate or space represents a different sampling location. The pattern provides for different sampling locations or provides for different spatial locations of the probe 12 to be used for different orientations. The pattern includes translation and/or rotation of the nuclear probe 12 to acquire data along beams from different locations and/or rotations relative to the patient. The pattern corresponds to positions and/or angles for receiving the radiation along lines in a volume of the patient.

The pattern is regularly spaced. The regular spacing is for the lines within the patient, intersection of the lines with the patient surface, and/or for the positions to detect radiation from the patient. By using the robotic assembly 11, the nuclear probe 12 may be positioned to scan at a regular spacing. Projections along lines with a known spacing along one or two dimensions may be provided. Projections along lines with known angle increments may be provided. Regular spacing may lead to more efficient image reconstruction. The pattern may be at a desired density. Lesser density may be used for more rapid scanning for radiation. Greater density may be used for less rapid scanning for radiation. Irregular spacing may be used, such as where the irregular pattern provides for increased information content for desired regions.

The processor 30 calculates the pattern or selects the pattern from a library. Alternatively, a template pattern is provided or selected and modified. The pattern may be based on the three-dimensional surface of the patient. Different patients have different surfaces. These differences are accounted for in establishing the pattern. Using the three-dimensional surface from the scanner 19, the positions of the nuclear probe 12 for radiation detection are set. For example, each position is a given distance (e.g., 5-20 cm) away from the surface. The distance is based on a normal to the surface for each location or is based on the beam distance given an orientation of the nuclear probe 12. For example, the probe 12 is always oriented for one pass at vertical, so the distance is from the vertical. Given a desired sampling density and the distance, the probe 12 locations are determined in three-dimensional space. As another example, the probe 12 is used at different angles for each location, so the normal to the three-dimensional surface is used for distance.

The surface model from the scanning system 24 is transferred to the processor 30. Based on the surface model, the path is computed, and the robotic assembly is controlled to automatically move the probe 12 to scan the patient. The automatic procedure may be programmed to have an optimal spacing in both translation and orientation to provide as complete as possible set of measurements for reconstruction.

FIG. 1 shows a regular grid 16 of sample locations around a patient. The angle for each location is at the normal to the surface of the patient. Alternatively, other angles are used. More than one sampling angle may be provided at one or more of the locations. FIG. 2 shows another pattern 16. The nuclear probe 12 is translated along lines at a given distance from the patient, continuously detecting radiation. The angle of the probe 12 changes based on the surface, changes for different passes along a given line, is held the same, or otherwise varies during the linear pass. The result is a plurality of line projections readings or a one-dimensional scan of the patient. Other patterns may be used.

The processor 30 determines an optimized path of travel for the pattern. For example, the nuclear probe 12 is positioned at locations along a given line over the surface. The probe 12 is positioned at discrete locations along the line in sequence. The probe 12 is then translated to the next parallel or other line. The lines may have any orientation relative to the patient. Given the capabilities of the robotic assembly 11, the most time efficient approach to moving the probe 12 for sampling may be used. The processor 30 calculates an optimum pattern and path of travel to sample the pattern.

The movement of the nuclear probe 12 is relative to the three-dimensional surface without contacting the patient. The three-dimensional surface is used to determined coordinates in the pattern without contacting the patient with the probe 12. The path of travel also avoids contact with the patient. With inclusion of the 3D scanner 19, the need for touching the skin at any or all times may be removed. The radiation scanning procedure may be faster and safer.

The movement is steady, with pauses to detect radiation. Between detection, the robotic assembly 11 moves the probe 12 to the next location in the pattern. In alternative embodiments, the detection of radiation is synchronized with the heart or breathing cycle. Using ECG signals and/or a breathing detector, the radiation at each location in the pattern may be detected at a particular phase of the physiological cycle. The surface is identified at the same phase of the cycle. Alternatively, the detection and surface identification are performed without regard to the phase of any physiological cycles.

In one embodiment, the processor 30 establishes the pattern as a function of a region of interest. The user indicates or the processor 30 detects a region of interest on the surface and/or within the volume of the patient. For example, the user indicates the region of interest as an area of the surface of the patient. The user outlines or assists the processor 30 in outlining an area on the three-dimensional surface.

The processor 30 creates the pattern based on the region of interest. The pattern samples the region of interest or is limited to the region on the surface and does not sample or have lines through the surface outside the region. In other embodiments, a greater density sampling is provided in the region and a lesser density sampling is used outside the region of interest. FIG. 1 shows lines of the pattern 16 on only a portion of the surface of the patient. The pattern 16 is limited to the region indicated by the user.

Figure 4:
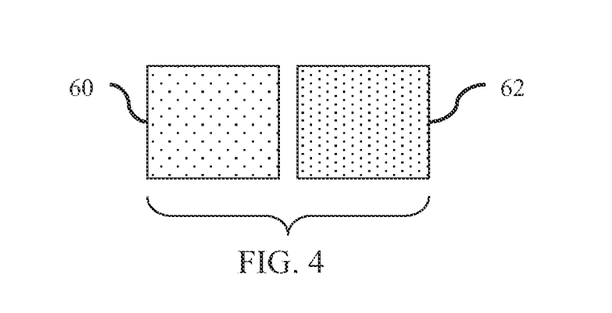
FIG. 4 is an illustration showing different example patterns for movement associated with different resolutions.

The processor 30 may set the pattern based, at least in part, on other user input. The robotic assembly 11 is controlled to perform the scan for radiation based on the user input. For example, the user selects a quality, density, time, or other setting. The selected setting changes the pattern. A lesser quality but more rapid scan may be provided by decreasing the sampling density. A higher quality but slower scan may be provided by increasing the sampling density. Assuming a regular grid of line entry points on the surface, FIG. 4 shows lesser density pattern 60 and a higher density pattern 62 on a flat surface. The selection may be for independently setting parameters for different regions, such as higher or lesser density in different regions, in a region of interest, or other variation. The pattern may include different sampling densities.

In one example, the user selects one sampling density for a given situation. A patient may have an invasive or spreading type of cancer, so the density is selected to be higher. For another patient, the sampling may be lower, such as for speeding up the scanning time. The density is different for different patients, different for the same patient at different times, and/or different for different regions of a same patient at a same time. Alternatively, the density or other pattern associated characteristic is the same for different patients, times, or regions.

Based on the user input, the robotic assembly 11 is controlled to perform the scan at different resolutions and corresponding speeds of the scan. The use of robotic assembly 11 may enable scanning procedures at different speeds, different accuracies (e.g., different resolutions), different quality (e.g., regular sampling instead of varied sampling), or combinations thereof. As compared to manual positioning, both faster and more accurate overall scanning may be provided in a same procedure.

The robotic assembly 11 allows repetition at a same resolution, same pattern, or other characteristics kept the same. The processor 30 controls the robotic assembly 11 to perform the same scan at different times, such as prior or during a surgical operation and then again after the surgical operation. Assuming a similar patient surface, the same pattern may be applied for the repetition. With a different patient surface, such as due to repositioning, the pattern may be the same, but with a different orientation relative to the patient. In other embodiments, a different pattern is used, but with a same or similar sample density.

By performing at the same resolution, pre and post operative information may be more easily compared. For example, post operative scanning may indicate residual radiation at a radiation location that was resected during the operation. The processor 30 may generate an image showing differences or similarities to highlight the lack of change or highlight the change. By basing the scans at different times on the same parameters, made available by automated control as compared to manual repetition, the successful resecting of undesired tissue may be confirmed. The accuracy provided by the same sampling or resolution may better reflect whether a change in radiation uptake has resulted.

The processor 30 is configured to tomographically reconstruct an image representing the volume. The reconstruction is from the radiation projections of the regularly spaced lines of the pattern. Using the collected measurements at different translations and/or orientations, image reconstruction is performed using any now known or later developed process. The translation and orientation measurements are readily available from the robotic arm, allowing precise and regular positioning of the projection information.

The reconstruction may be one or two-dimensional. The probe 12 is moved in a plane or along a curved surface. For each sample location along the plane or surface, a measurement of radiation along an orthogonal line is made. Using the relative positions determined from the pattern, the relative position of each measurement is provided. The relative position of the measurement lines or regions is mapped. A regular sampling may be interpolated. A two-dimensional set of data is provided where the magnitude at each location represents the radiation along an orthogonal line and the probe is moved in two dimensions.

Since a nuclear activity probe 12 produces a one-dimensional reading, the probe's motion is used to reconstruct either a 2D or a 3D SPECT image from the data acquired by the detector. The motion information, such as in the form of the pattern of sampling locations, may be directly utilized for SPECT reconstruction of nuclear data. The location information is provided by the processor 30, the robotic assembly 11, and/or the three-dimensional scanner system 24.

In one embodiment, a three-dimensional reconstruction is assisted by data from lines at different angles. As the probe 12 is translated, the probe 12 may also be tilted to different angles. As a result, depth information may be derived. Each voxel location contributes to measurements by the detector at different times. These locations are distributed in three-dimensions in the volume. The tilt angles for the measurements and position information may be used to reconstruct the distribution of radiation. Any tomographic reconstruction process may be used, such as filtered back projection or iterative reconstruction.

The processor 30 may reconstruct the image using the three-dimensional surface in addition to the pattern. The view from the three-dimensional scanner 19 may be used to limit the possible locations of the radiation in the reconstruction. The surface is a boundary for the radiation. By including the surface in the reconstruction, more efficient or rapid reconstruction may be provided.

The processor 30 uses the reconstructed volume for generating an image. The reconstructed volume represents the radiation at different voxels. The voxels may be used to generate a rendering of the volume to an image. Alternatively, the reconstruction is of a two-dimensional image without reconstructing to the volume. The generated image is output for display.

The processor 30 may process the reconstructed data and/or the image. For example, filtering, interpolation, decimation, segmenting, highlighting, graphical overlays or other processing is performed.

The processor 30 may generate a comparison of images from different scans for radiation. The reconstructed data for one scan may be from a scan prior to or during a surgical procedure and the reconstructed data for another scan may be from a scan after the surgical procedure. To provide a comparison, the processor 30 generates images from the different scans for simultaneous display. The images are shown to the user at a same time for comparison. Alternatively, the images or reconstructed data are combined for comparison. For example, data from one scan is subtracted from data for another scan, highlighting differences. An image showing the differences is generated for display.

Other combinations are possible. Spatially aligned data may be combined by summing, averaging, alpha blending, maximum selection, minimum selection or other process. Alternatively, separate images are generated for each scan or for a representative scan.

The processor 30 may combine functional and diagnostic information. For example, the functional information from radiation detection is represented by a color or graphic overlay on an anatomical image. Locations associated with detected radiation above a certain amount are highlighted in a spatially aligned diagnostic image.

The memory 32 is a graphics processing memory, a video random access memory, a random access memory, system memory, random access memory, cache memory, hard drive, optical media, magnetic media, flash drive, buffer, database, combinations thereof, or other now known or later developed memory device for storing data or image information. The memory 32 is part of an imaging system, part of a computer associated with the processor 30, part of a database, part of another system, or a standalone device.

The memory 32 stores one or more datasets representing detected radiation projections, volume or image reconstruction, images, comparison information, identified patient surface, and/or three-dimensional scanner images. Data from different scans with the probe 12 at different locations is stored for reconstruction. The surface coordinates are stored for using in control of motion of the robotic assembly 11. Templates or selectable patterns may be stored.

Other types of data may be stored, such as pre-operative diagnostic scan data (e.g., ultrasound, x-ray, computed tomography, magnetic resonance, or positron emission). For example, CT or MRI data is acquired prior to intervention, such as just prior to (same day) or during a previous appointment on a different day. The data represents tissue, preferably in a high resolution.

Other types of data include scan parameters for previous scans, such as the pattern used. The stored scan parameters may allow repetition of the same or similar scan or radiation detection with a same or similar resolution. By storing resolution related parameters, more easily comparable data from scans performed at different times may result.

The memory 32 or other memory is a non-transitory computer readable storage medium storing data representing instructions executable by the programmed processor 30 for robotic navigation in nuclear probe imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 34 is a monitor, LCD, projector, plasma display, CRT, printer, or other now known or later developed devise for outputting visual information. The display 34 receives images, graphics, or other information from the processor 30, memory 32, three-dimensional scanning system 24, or SPECT system 22.

The display 34 provides one or more images representing anatomy and/or function. The images may be a combination of multiple sources of information, such as representing anatomy highlighted in color based on function. The images may be for comparison. The images may be a combination of data from scans at different times. The images are reconstructed planar images from a scanned volume, are two-dimensional planar images as scanned, and/or are three-dimensional renderings. The image may be a rendering of the three-dimensional surface of the patient. An image from the three-dimensional scanning system 24 may be output adjacent to, overlaid with, or combined with functional imaging information from the radiation detection. In other embodiments, the display 34 is part of a smart phone or other mobile computing device.

In an alternative embodiment, the display 34 is a head mounted display. Images representing augmented reality are displayed. For example, functional imaging information (e.g., detected radiation uptake), three-dimensional surface information, or both are displayed adjacent to or overlaid on live video images of the patient or overlaid on a screen so that the overlays appear in alignment with a live view of the patient. During an interventional procedure, a physician may view images of the acquired and segmented radiation data fused with a current view of the patient. This may assist the physician with visual cues and guidance for an ongoing operation.

FIG. 4 shows a method for robotic navigation in nuclear probe imaging. The method is implemented by the robotic assembly 11, nuclear probe 12 and/or three-dimensional scanner 19 of FIG. 1 or 2, the system of FIG. 3, or another system. The acts are performed in the order shown or other orders. Additional, different, or fewer acts may be provided. For example, the display act 54 is not provided, but instead the reconstruction is used to control therapeutic application. As another example, acts 40 and/or 44 are not provided.

Figure 5:
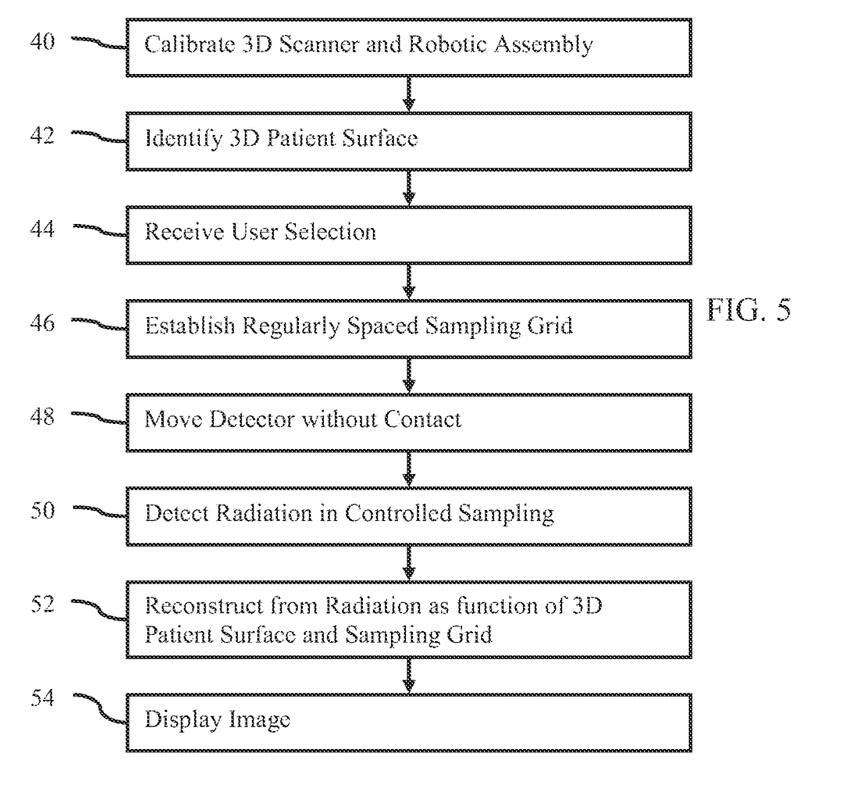
FIG. 5 is a flow chart diagram of one embodiment of a method for robotic navigation in nuclear probe imaging.

In act 40, the coordinate system for the three-dimensional surface scanning system is calibrated with the coordinate system for the robotic assembly and corresponding nuclear detector. The detector is positioned to different locations within the view of the three-dimensional scanner. The coordinates of each system at each of the plurality of locations is determined. A transform between the coordinates is calculated. The calibration provides a spatial transform relating the locations for any three-dimensional surface with the locations for moving of the detector.

The calibration occurs prior to use with a patient. The calibration may be performed once the overall system is assembled and repeated as needed. The calibration may be periodically tested and updated if desired.

In act 42, a three-dimensional surface of a patient is identified. The surface of a patient is determined from a camera. The camera, alone or in combination with other devices, determines the spatial locations of the patient skin in three-dimensions rather than a mere two-dimensional view. Using time-of-flight, stereo view, or other mechanism, the locations within three-dimensions of the surface of the patient are determined.

In act 44, user selection is received. The user inputs information for detecting radiation or interacting with the patient. A processor or other component receives the user selection.

In one embodiment, the user selection of a region of interest in the three-dimensional surface is received. An image of the surface is rendered to a display. By tracing or point selection, the user indicates a region of interest. The region of interest is a sub-region of the identified surface. Alternatively, the user selection is received by control of the field of view of the camera or other surface detection system.

In an alternative or additional embodiment, the user indication of resolution selection is received. A menu selection, list selection, numerical input, slider or knob setting, or other user interface is presented to the user. The user selects the resolution to be used for detecting radiation.

The resolution selection may be presented to the user as any of various types of parameters. Any characteristic resulting in a change of resolution may be considered a setting of the resolution. For example, user selection of a resolution, quality, speed, or combinations thereof is received. Since higher resolutions require more sample locations or density of sampling, the higher resolutions may be associated with slower speeds of the scan. Similarly, higher quality may be associated with greater resolution.

Other user selections or inputs may be received. For example, the user indicates the type or format of the display. Other parameters for the scan by the nuclear detector may be set by the user, such as the range of angles, the distance away from the patient to be used for detecting radiation, and/or a rate of movement between sample locations.

In act 46, regularly spaced locations are established. Regular spacing includes evenly spaced, such as all adjacent sample locations being spaced apart by a same distance orthogonal to the normal with the surface and all angles being separated by the same amount. Regular spacing may include variance in the spacing, but with a predictable or known pattern, such as more density of evenly spaced sample locations in a region of interest and decreasing density as a function of distance away from the region of interest.

The locations are for lines in the volume of the patient, points of intersection with the surface of radiation detection lines from the detector into the volume, and/or for locations of the probe during detection. A location at a three-dimensional coordinate position may be associated with different angles of incidence of the projection line for radiation detection. By varying the angle, additional sampling locations result.

The locations are established based on a region to be scanned. The region may be a segmented portion of the patient, such as identifying breast tissue in an x-ray or computed tomography image or identifying a portion of the three-dimensional surface associated with the breast. The region may be indicated by the user, such as a region of interest. For example, the user may indicate a region of interest on an image of the surface. The surface is associated with a top of the region and the volume beneath the surface for a set distance or to the patient table defines the volume of interest.

Given the spatial boundary for detecting radiation, the number of angles along which linear projections are to be acquired is determined. The number may be user settable, based on speed, resolution, or quality selections, or predetermined. The pattern may be limited to be acquired from non-interfering locations of the robotic assembly, such as avoiding sampling from locations where a physician is to work.

Given the spatial boundary for detecting radiation, the density or sampling distribution of locations is determined. Based on speed, quality, resolution and/or predetermined templates, the distribution within the volume is determined. For example, fifty locations are to be sampled at a given angle along one dimension. Where the volume extends 10 cm along that dimension, then the locations are established at every 20 mm. As another example, the density is established and then fit to the volume, such as desiring 30 mm sample interval so that 40 locations are set for 12 cm length along a given dimension.

The pattern for each possible angle is the same or different. For example, the pattern is set based on coordinates and then repeated for different angles. Alternatively, the patterning for the angles is established with the coordinates in a comprehensive pattern.

The user selection of the region of interest, field of view, density, number of angles, resolution, quality or other setting may be used to establish the pattern. Alternatively, the pattern is set based on processor determined information.

Where the pattern is not for the detector itself, the pattern is extrapolated to determine detector locations. The pattern for the detector accounts for the surface of the patient. The locations in the pattern for the detector are spaced from the patient surface by a same amount or predetermined amounts for each location. In alternative embodiments, different distances for different locations may be used.

In act 48, a detector is moved to the regularly spaced locations. The detector is moved to cover the pattern. The detector is translated and/or rotated about the patient. The detector is moved to sample at each location in the pattern. Since the pattern is established, in part, on the resolution setting, the movement to sample at the different locations is a function of the resolution.

Any path of travel may be used, such as detecting at different angles at each location before moving to another location and moving between locations along a line before shifting to another line. In other examples, a region growing approach is used where any unsampled adjacent locations are sampled before moving to an unsampled adjacent position.

Since the locations are based on the distance away from the surface, the movement is based on the three-dimensional surface. Further consideration may be used, such as assuring that the movement does not result in the detector intersecting with the surface between positions. The detector is moved about the patient based on the three-dimensional surface to avoid contact with the patient.

In act 50, radiation is detected. The detector detects radiation at the regularly spaced locations. At each of the locations, the detector is activated or allowed to detect radiation for a time. Any time may be used. The detector is deactivated for moving to other locations. Alternatively, the detector continues to detect as moved. The location of the detector, angle of the detector, and corresponding line or beam within the volume is associated with any detected radiation.

The detector is aimed such that the radiation being detected is from within the patient. The radiation is detected along a beam at each of the regularly spaced locations. Radiation projection information is received from the nuclear probe for different positions.

The sources of radiation are taken up, transferred, or pooled, showing the function of anatomy. For example, the amount of tracer taken up by brain tissue indicates the functioning of the brain tissue. As another example, distribution of the tracer in the cardiac system shows operation of the cardiac system. In other embodiments, the tracers are tagged to bind to or otherwise collect based on function. For example, the radionuclides bind to cancer or show glucose uptake. Any now known or later developed functional imaging may be used.

The level or magnitude of radiation along lines at different locations is detected. Radionuclides, radioactive tracer, or other sources of radiation in the patient generate positrons or gamma rays. The detector senses the gamma rays or other radiation. The detector detects radiation along a line, such as a cone shaped region extending from the detector. As the detector moves, the radiation at different locations is measured. The measurements provide a two-dimensional map of radiation emitted in a projection along a third dimension or a one-dimensional map of radiation emitted in a projection along a plane.

With rocking or tilting of the detector, measurements for projections through the same volume, but at different angles, are obtained. These measurements may be converted into a three-dimensional map of radiation emission, providing measurements in three-dimensions instead of projections along one or two dimensions.

For converting the projection information into data representing a plane or volume, an image may be reconstructed in act 52. The radiation projection information is used to reconstruct the radiation from different voxels, pixels, or locations within the patient rather than along lines. The projections of the radiation along the beams are reconstructed into data representing points, pixels, or voxels. While radiation from different locations in the volume or plane is reconstructed, this reconstruction may be referred to as image reconstruction. The reconstructed plane or volume may be used to generate an image.

The reconstruction uses the spatial information for each projection. The location of the line associated with the projection is used. Since the robotic assembly provides for sampling regularly spaced locations, the reconstructed data may have a better quality, be performed more accurately, and/or be performed more efficiently. In addition to the projection locations, the three-dimensional surface may be used in the reconstruction. The surface indicates a boundary for the radiation. The radiation is from within the patient, not outside the patient. The location of the radiation is limited during reconstruction. This limitation may speed the reconstruction and/or result in better quality reconstruction.

In act 54, an image of the reconstructed volume is displayed. The image represents radiation at different locations. The image is rendered from the volume data, such as using maximum intensity, alpha blending, or other rendering from a given viewing direction. The viewing direction may be from the three-dimensional scan camera view point, from a physicians view point, or from other view points.

Alternatively, the image is a two-dimensional reconstruction. By moving the detector to different locations, a two-dimensional map of hotspots may be created. The image of the two-dimensional map is generated. Optionally, the positions of the hotspots are identified, such as by image processing or thresholding. The detector is moved to acquire radiation along different lines at different angles through each of the hotspots. A three-dimensional reconstruction may be formed from the radiation along these lines. This reconstruction represents the volume of the patient. The reconstructed data may be registered with preoperative PET or SPECT scans.

Other images may be displayed with the functional or radiation image. For example, a rendering of the three-dimensional surface from the same perspective is displayed adjacent to the radiation image. Preoperative images, such as from computed tomography, magnetic resonance, or ultrasound, may be displayed.

In one embodiment, the radiation image is combined with another image. For example, radiation images from different times but a same perspective are combined by addition, subtraction, or overlay. The different times may be prior to, during, and/or after a surgical procedure, such as combining an image from prior to the procedure with an image after the procedure. In another example, the radiation image is combined with an image of the three-dimensional surface. The combined image is displayed to the user.

Real-time 2D/3D SPECT from the nuclear probe may be fused with pre-acquired PET and/or SPECT datasets from 3D tomographic scanners. This may be useful in order to get a better delineation of lesions, by matching approximate SPECT reconstructions from the real-time robotically positioned probe with accurate PET/SPECT reconstructions from 3D tomography.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for robotic navigation in nuclear probe imaging, the system comprising:
 a nuclear detector for detecting radiation, wherein the nuclear detector is operable to receive radiation projection along a line;
 a robotic assembly connected with the nuclear detector, the robotic assembly operable to move the nuclear detector relative to a patient;
 a three-dimensional scanner positioned to view the patient; and
 a processor configured to control movement of the robotic assembly to scan the patient with the nuclear detector in a pattern, the movement being a function of the view of the patient by the three-dimensional scanner, the pattern corresponding to positions and angles for receiving the radiation along lines regularly spaced in a volume of the patient, the processor being configured to tomographically reconstruct an image representing the volume from the radiation projections of the regularly spaced lines, the image tomographically reconstructed with the positions and angles and additionally a three-dimensional surface provided in the view from the three-dimensional scanner as a boundary of the patient limiting radiation locations to one side of the boundary in the reconstruction.

2. The system of claim 1 wherein the robotic assembly comprises a robot arm connected with the nuclear detector and a base configured to be stationary during movement of the robot arm and relative to the three-dimensional scanner.

3. The system of claim 1 wherein the robotic assembly comprises a raster scanner comprising a pan and a tilt stage, the nuclear detector moveable within the pan.

4. The system of claim 1 wherein the nuclear detector comprises a gamma detector.

5. The system of claim 1 further comprising a user input, wherein the processor is configured to control the robotic assembly to perform the scan at different resolutions and corresponding speeds of the scan as a function of a user selection from the user input.

6. The system of claim 1 wherein the processor is configured to control the robotic assembly for performing the scan at a first sampling density for the patient and at a second sampling density different than the first sampling density for a different patient.

7. The system of claim 1 further comprising a memory, the memory configured to store parameters of the scan, the parameters including a resolution, the scan performed prior to or during a surgical operation, and wherein the processor is configured to repeat the scan after the surgical operation, the repeat being based on the same parameters, and configured to generate a first image from the scan performed prior to or during the surgical operation and a second image from the scan performed after the surgical operation, the first and second images displayed simultaneously or combined.

8. The system of claim 1 wherein the processor is configured to perform the scan at different times using the pattern for each and to generate a comparison of images resulting from the scans.

9. The system of claim 1 wherein the processor is configured to determine a three-dimensional surface of the patient from the view of the patient, the movement being of the nuclear detector relative to the three-dimensional surface without contacting the patient based on the three-dimensional surface.

10. The system of claim 1 wherein the processor is configured to establish the pattern as a function of a region of interest indicated from the view of the patient.

11. The system of claim 10 further comprising a display configured to display an image of the view, the image representing a three-dimensional surface of the patient, and a user input configured to receive indication of the region of interest on the patient indicated from the three-dimensional surface, and wherein the pattern includes translation and rotation of the nuclear detector to acquire data along beams from different locations and rotations relative to the three-dimensional surface.

12. The system of claim 1 wherein the processor is configured to calibrate the robotic assembly with the three-dimensional scanner.

13. A method for robotic navigation in nuclear probe imaging, the method comprising:
identifying a three-dimensional surface of a patient;
moving a detector to regularly spaced locations about the patient based on the three-dimensional surface, the moving avoiding contact with the patient;
detecting radiation with the detector at the regularly spaced locations, the detector aligned such that the radiation being detected is from within the patient; and
reconstructing an image from the radiation with the regularly spaced locations and additionally the three-dimensional surface as a patient boundary limiting locations of the radiation to one side of the patient boundary in the reconstructing, the image representing the patient; and
displaying the reconstructed image.

14. The method of claim 13 further comprising:
calibrating a coordinate system for the detecting of the three-dimensional surface with a coordinate system for the moving of the detector;
wherein moving comprises translating and rotating the detector about the patient based on the three-dimensional surface;
wherein detecting comprises detecting along a beam at each of the regularly spaced locations; and
wherein reconstructing comprises reconstructing from projections of the radiation along the beams, the reconstructing being a function of an orientation of the detector at each of the regularly spaced locations.

15. The method of claim 13 wherein identifying, moving, detecting, and reconstructing are performed prior to or during a surgical procedure;
further comprising:
repeating the identifying, moving, detecting and reconstructing with the same regularly spaced locations after the surgical procedure; and
displaying another image from the repetition for comparison with the image from prior to or during the surgical procedure.

16. The method of claim 13 further comprising:
receiving user selection of a resolution, quality, speed, or combinations thereof; and
establishing the regularly spaced locations as a function of the user selection.

17. The method of claim 13 further comprising:
receiving user selection of a region of interest in the three-dimensional surface; and
establishing the regularly spaced locations as a function of the region of interest.

18. The method of claim 13 wherein reconstructing comprises reconstructing a two-dimensional single photon emission computed tomography image.

19. The method of claim 18 wherein moving the detector comprises moving the detector for a two-dimensional map of positions of hotspots;
further comprising:
identifying the positions and moving the detector to acquire radiation along lines at different angles through the positions; and
computing a three-dimensional reconstruction from the radiation.

20. In a non-transitory computer readable storage medium having stored therein data representing instructions executable by a programmed processor for robotic navigation in nuclear probe imaging, the storage medium comprising instructions for:
determining a surface of a patient from a camera;
receiving a user indication of resolution selection;
robotically positioning a nuclear probe as a function of the resolution selection, wherein the robotically positioning is performed as a function of the surface such that the nuclear probe is positioned around the surface without contacting the patient;
receiving radiation projection information from the nuclear probe for different positions from the positioning; and
reconstructing an image from the radiation projection information, projection line spatial information, and additionally the surface as a patient boundary limiting locations of radiation to one side of the patient boundary in the reconstructing.

21. The non-transitory computer readable storage medium of claim 20 wherein reconstructing comprise reconstructing a two-dimensional image.

* * * * *